US011224347B2

(12) United States Patent
Sato et al.

(10) Patent No.: US 11,224,347 B2
(45) Date of Patent: Jan. 18, 2022

(54) BIOMETRIC INFORMATION MEASUREMENT SYSTEM AND BIOMETRIC INFORMATION MEASUREMENT APPARATUS

(71) Applicant: Agama-X Co., Ltd., Tokyo (JP)

(72) Inventors: Masahiro Sato, Kanagawa (JP); Motofumi Baba, Kanagawa (JP); Monta Ido, Kanagawa (JP); Masayoshi Nakao, Kanagawa (JP); Kengo Tokuchi, Kanagawa (JP)

(73) Assignee: Agama-X Co., Ltd., Tokyo (JP)

( * ) Notice: Subject to any disclaimer, the term of this patent is extended or adjusted under 35 U.S.C. 154(b) by 107 days.

(21) Appl. No.: 16/538,841

(22) Filed: Aug. 13, 2019

(65) Prior Publication Data
US 2020/0288986 A1    Sep. 17, 2020

(30) Foreign Application Priority Data
Mar. 12, 2019  (JP) .............................. JP2019-045117

(51) Int. Cl.
*A61B 5/0205*    (2006.01)
*A61B 5/021*    (2006.01)
(Continued)

(52) U.S. Cl.
CPC ............ *A61B 5/0205* (2013.01); *A61B 5/165* (2013.01); *A61B 5/374* (2021.01); *A61B 5/4812* (2013.01);
(Continued)

(58) Field of Classification Search
CPC ....... A61B 5/0205; A61B 5/021; A61B 5/024; A61B 2562/0219; A61B 5/0022;
(Continued)

(56) References Cited

U.S. PATENT DOCUMENTS 6,163,723 A * 12/2000 Roberts .............. A61N 1/36585
607/18
10,215,619 B1 * 2/2019 Kovacs .................. G01G 19/50
(Continued)

FOREIGN PATENT DOCUMENTS

JP          4575133        11/2010
JP        2011217986       11/2011

OTHER PUBLICATIONS

Hiroaki Takatsu et al., "An Evaluation of the Quantitative Relationship between the Subjective Stress Value and Heart Rate Variability", T.IEE Japan, vol. 120-C, No. 1, Jan. 2000, pp. 104-110.

*Primary Examiner* — Carl H Layno
*Assistant Examiner* — Anh-Khoa N Dinh (57) ABSTRACT

A biometric information measurement system includes a first measurement apparatus, a second measurement apparatus, and a control apparatus. The first measurement apparatus measures first biometric information of a subject. The second measurement apparatus measures second biometric information which is biometric information of the subject and which is different from the first biometric information. The control apparatus changes a condition of measurement performed by the second measurement apparatus on the basis of the first biometric information.

13 Claims, 2 Drawing Sheets (51) Int. Cl.
  *A61B 5/024* (2006.01)
  *A61B 5/00* (2006.01)
  *A61B 5/16* (2006.01)
  *A61B 5/374* (2021.01)
(52) U.S. Cl.
  CPC ............ *A61B 5/7405* (2013.01); *A61B 5/746* (2013.01); *A61B 5/021* (2013.01); *A61B 5/024* (2013.01); *A61B 2562/0219* (2013.01)
(58) Field of Classification Search
  CPC ......... A61B 5/0024; A61B 5/11; A61B 5/165; A61B 5/374; A61B 5/4812; A61B 5/7405; A61B 5/746
  See application file for complete search history.

(56) References Cited

U.S. PATENT DOCUMENTS

| | | | | |
|---|---|---|---|---|
| 2005/0240087 A1* | 10/2005 | Keenan | .................. | A61B 5/721 600/301 |
| 2006/0200009 A1* | 9/2006 | Wekell | .................. | G16H 40/67 600/300 |
| 2009/0082692 A1* | 3/2009 | Hale | ...................... | A61B 5/165 600/544 |
| 2015/0173631 A1* | 6/2015 | Richards | ............ | A61B 5/02427 600/479 |

* cited by examiner

FIG. 2

BIOMETRIC INFORMATION MEASUREMENT SYSTEM AND BIOMETRIC INFORMATION MEASUREMENT APPARATUS

CROSS-REFERENCE TO RELATED APPLICATIONS

This application is based on and claims priority under 35 USC 119 from Japanese Patent Application No. 2019-045117 filed Mar. 12, 2019.

BACKGROUND

(i) Technical Field

The present disclosure relates to a biometric information measurement system and a biometric information measurement apparatus.

(ii) Related Art

There has been known technology for measuring biometric information such as electroencephalogram (EEG).

Japanese Unexamined Patent Application Publication No. 2011-217986 describes technology for measuring EEG by providing an electrically conductive member in a canal-type earphone.

By the way, it is conceivable to measure a plurality of pieces of biometric information using a plurality of measurement apparatuses. However, in the case where a plurality of measurement apparatuses are used, more electric power is consumed than in the case where one measurement apparatus is used.

SUMMARY

Aspects of non-limiting embodiments of the present disclosure relate to reducing power consumption in the case of measuring biometric information using a plurality of measurement apparatuses than in the case where all the measurement apparatuses measure biometric information in accordance with a fixed measurement condition.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided a biometric information measurement system including a first measurement apparatus, a second measurement apparatus, and a control apparatus. The first measurement apparatus measures first biometric information of a subject. The second measurement apparatus measures second biometric information which is biometric information of the subject and which is different from the first biometric information. The control apparatus changes a condition of measurement performed by the second measurement apparatus on the basis of the first biometric information.

BRIEF DESCRIPTION OF THE DRAWINGS

An exemplary embodiment of the present disclosure will be described in detail based on the following figures, wherein.

DETAILED DESCRIPTION

Figure 1:
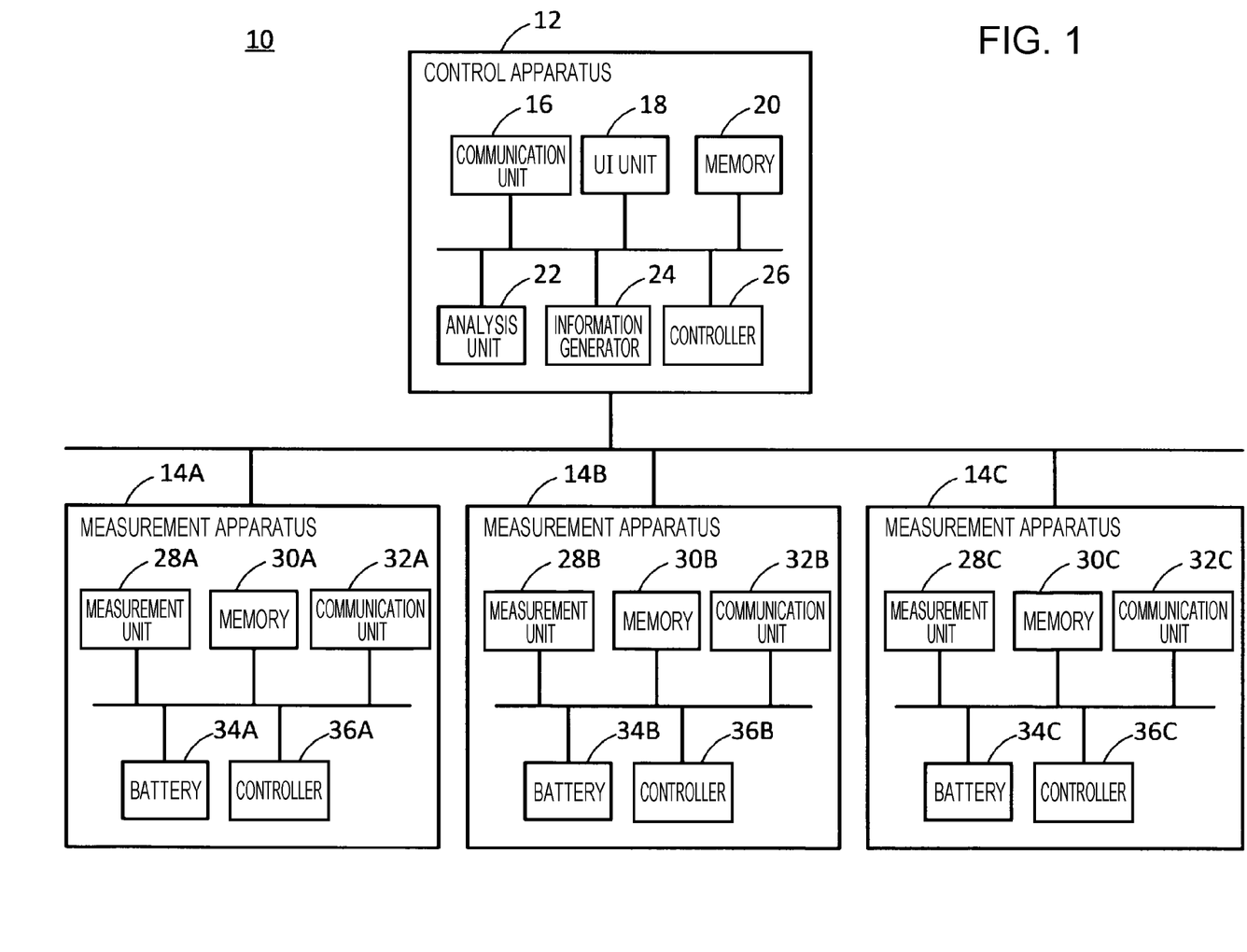
FIG. 1 is a block diagram illustrating the configuration of a biometric information measurement system according to an exemplary embodiment of the present disclosure.

Hereinafter, the configuration of a biometric information measurement system according to an exemplary embodiment of the present disclosure will be described with reference to FIG. 1. FIG. 1 illustrates an example of the configuration of the biometric information measurement system according to the present exemplary embodiment.

A biometric information measurement system 10 according to the present exemplary embodiment includes, for example, a control apparatus 12 and a plurality of measurement apparatuses. In the example illustrated in FIG. 1, the biometric information measurement system 10 includes three measurement apparatuses. Specifically, the biometric information measurement system 10 includes measurement apparatuses 14A, 14B, and 14C. Hereinafter, the measurement apparatuses 14A, 14B, and 14C will be collectively referred to as the "measurement apparatuses 14" when it is unnecessary to distinguish between them. The configuration illustrated in FIG. 1 is only one example, and the number of measurement apparatuses 14 included in the biometric information measurement system 10 may be two, or four or more. In addition, the biometric information measurement system 10 may include a plurality of control apparatuses 12, or may include an external apparatus such as a server.

Transmission and reception of information between the control apparatus 12 and each measurement apparatus 14 may be realized by wired communication or wireless communication. The control apparatus 12 and each measurement apparatus 14 may be physically connected to each other by a cable to transmit and receive information to and from each other, or may transmit and receive information to and from each other through wireless communication. As the wireless communication, Wi-Fi (registered trademark) or short-distance wireless communication may be used. As the short-distance wireless communication, for example, Bluetooth (registered trademark), near field communication (NFC), or radio-frequency identification (RFID) may be used. Alternatively, the control apparatus 12 and each measurement apparatus 14 may communicate with each other through a network such as a local area network (LAN). Note that the control apparatus 12 may transmit and receive information using the Internet. In addition, the measurement apparatuses 14 may transmit and receive information using the Internet.

The control apparatus 12 is configured to control the operation of each measurement apparatus 14. The control apparatus 12 is, for example, a personal computer (hereinafter abbreviated as "PC"), a tablet PC, a smartphone, or a cellular phone. The control apparatus 12 may be mobile terminal apparatus such as a tablet PC, a smartphone, or a cellular phone.

The measurement apparatuses 14 are configured to measure biometric information of a subject. Each measurement apparatus 14 is configured to measure, for example, a different type of biometric information from the other measurement apparatuses 14. Needless to say, all or some of the measurement apparatuses 14 may be configured to measure the same type of biometric information. In addition, each measurement apparatus 14 may be configured to measure one type of biometric information, or may be configured to measure a plurality of types of biometric information.

The measurement apparatuses 14 may be wearable apparatuses such that the entire measurement apparatuses 14 are worn by a subject, or may be apparatuses that measure biometric information by having an electrode or the like worn by a subject.

Biometric information includes various types of physiological information and anatomical information obtained from a subject who is a living body. The scope of the concept of biometric information includes, for example, electroencephalogram (EEG), pulse rate, blood pressure, heart rate, movement of the subject, and the like. In addition, electrocardiogram (ECG) waveform, electromyogram (EMG) waveform, eye movement, and the like may be used as biometric information. Needless to say, these are only one example of biometric information, and other physiological information and anatomical information may be used as biometric information.

The control apparatus 12 is configured to control measurement performed by each measurement apparatus 14. In addition, the control apparatus 12 may control analysis, storage, or output of biometric information on receipt of biometric information from each measurement apparatus 14. For example, the control apparatus 12 may control display of biometric information or transmission of biometric information to another apparatus as output of biometric information.

Note that one measurement apparatus 14 among the measurement apparatuses 14A, 14B, and 14C corresponds to an example of a "first measurement apparatus", and another or other measurement apparatuses 14 correspond to an example(s) of a "second measurement apparatus".

Next, the configuration of the control apparatus 12 will be described in detail.

A communication unit 16 is a communication interface, and has the function to transmit information to another apparatus and the function to receive information from another apparatus. The communication unit 16 may have a wired communication function or a wireless communication function. The communication unit 16 receives, for example, biometric information transmitted from the measurement apparatuses 14. In addition, the communication unit 16 may transmit various types of information to an external apparatus such as a server. For example, biometric information may be transmitted from the control apparatus 12 to an external apparatus.

A user interface (UI) unit 18 is a user interface unit, and includes, for example, a display and an operation unit. The display is a display device such as a liquid crystal display or an electroluminescence (EL) display. The operation unit is, for example, an input device such as a keyboard and a mouse. The UI unit 18 may be a user interface unit that serves as both a display and an operation unit (such as a touchscreen, or a display device that displays an electronic keyboard).

Memory 20 includes one or more storage areas that store information. Each storage area includes, for example, one or more storage devices (such as physical drives including a hard disk drive and memory). For example, biometric information measured by the measurement apparatuses 14 is stored in the memory 20.

An analysis unit 22 is configured to analyze biometric information measured by the measurement apparatuses 14. The analysis unit 22 may analyze biometric information using, for example, a known analyzing method.

An information generator 24 is configured to generate biometric information or other information on the basis of one or more pieces of biometric information. The information generator 24 may generate, on the basis of different pieces of biometric information, another new piece of biometric information.

A controller 26 is configured to control the operation of each unit of the control apparatus 12. The controller 26 is also configured to control measurement performed by each measurement apparatus 14.

The controller 26 controls, for example, measurement performed by the second measurement apparatus(es) on the basis of first biometric information measured by the first measurement apparatus. The first measurement apparatus is one measurement apparatus 14 among the measurement apparatuses 14A, 14B, and 14C. The second measurement apparatus(es) is/are one or more measurement apparatuses 14 among the measurement apparatuses 14A, 14B, and 14C. The second measurement apparatus(es) is/are an apparatus(es) that measures second biometric information different from the first biometric information.

The controller 26 may change, for example, a condition of measurement performed by the second measurement apparatus(es) on the basis of the first biometric information.

The condition of measurement performed by the second measurement apparatus(es) is, for example, a time interval of measurement performed by the second measurement apparatus(es). In other words, the controller 26 changes the time interval of measurement performed by the second measurement apparatus(es) on the basis of the first biometric information. The time interval of measurement is the time interval from a time point at which biometric information is measured to a time point at which next biometric information is measured. For example, in the case where the time interval of measurement is set to one minute, biometric information is measured every minute.

Note that a measurement period in which biometric information is measured and a non-measurement period in which no biometric information is measured may be alternatively defined. In this case, measurement and non-measurement of biometric information are alternately repeated. In other words, biometric information is measured in a measurement period; when the measurement period elapses, biometric information is not measured in a non-measurement period; and biometric information is again measured in the next measurement period.

In another example, the condition of measurement performed by the second measurement apparatus(es) may be the sensitivity of measurement performed by the second measurement apparatus(es). In other words, the controller 26 may change the sensitivity of measurement performed by the second measurement apparatus(es) on the basis of the first biometric information.

In yet another example, the condition of measurement performed by the second measurement apparatus(es) may be at least one of the start timing and the end timing of measurement performed by the second measurement apparatus(es). In other words, the controller 26 may change at least one of the start timing and the end timing of measurement performed by the second measurement apparatus(es) on the basis of the first biometric information.

Hereinafter, the configuration of the measurement apparatuses 14 will be described in detail.

The measurement apparatus 14A includes a measurement unit 28A, memory 30A, a communication unit 32A, a battery 34A, and a controller 36A.

The measurement apparatus 14B includes a measurement unit 28B, memory 30B, a communication unit 32B, a battery 34B, and a controller 36B.

The measurement apparatus 14C includes a measurement unit 28C, memory 30C, a communication unit 32C, a battery 34C, and a controller 36C.

The measurement units 28A, 28B, and 28C are configured to measure biometric information of a subject. The measurement units 28A, 28B, and 28C are configured to measure different types of biometric information of a subject. Needless to say, the measurement units 28A, 28B, and 28C may be configured to measure the same type of biometric information of a subject. Here, it is assumed that, for example, the measurement units 28A, 28B, and 28C measure different types of biometric information of a subject.

The memory 30A, 30B, and 30C includes one or more storage areas that store information. Each storage area includes, for example, one or more storage devices (such as physical drives including a hard disk drive and memory). For example, biometric information measured by the measurement unit 28A is stored in the memory 30A. The same applies to the memory 30B and 30C.

The communication units 32A, 32B, and 32C are communication interfaces, and have the function to transmit information to another apparatus and the function to receive information from another apparatus. The communication units 32A, 32B, and 32C may have a wired communication function or a wireless communication function. The communication units 32A, 32B, and 32C receive, for example, control information transmitted from the control apparatus 12, and transmit measured biometric information to the control apparatus 12. In addition, the communication units 32A, 32B, and 32C may transmit biometric information to an external apparatus such as a server. In this case, biometric information may be stored in the external apparatus. Note that biometric information may be stored in the control apparatus 12 or an external apparatus, instead of being stored in the memory 30A, 30B, and 30C.

In the case where biometric information is transmitted to an external apparatus and stored in the external apparatus, the control apparatus 12 may obtain the biometric information from the external apparatus, instead of obtaining the biometric information from the measurement apparatuses 14.

The battery 34A is configured to supply electric power to each unit of the measurement apparatus 14A. The battery 34B is configured to supply electric power to each unit of the measurement apparatus 14B. The battery 34C is configured to supply electric power to each unit of the measurement apparatus 14C. Alternatively, no battery may be provided in the measurement apparatuses 14, and electric power may be supplied from an external power source such as a commercial power source to the measurement apparatuses 14.

The controller 36A is configured to control the operation of each unit of the measurement apparatus 14A. The controller 36B is configured to control the operation of each unit of the measurement apparatus 14B. The controller 36C is configured to control the operation of each unit of the measurement apparatus 14C. For example, the controllers 36A, 36B, and 36C control the operation of the respective measurement apparatuses 14 under control of the controller 26 of the control apparatus 12. Note that each of the measurement apparatuses 14A, 14B, and 14C may be provided with a UI unit, and measured biometric information may be displayed on the UI unit. In addition, the user may use the UI unit to operate each of the measurement apparatuses 14A, 14B, and 14C.

Note that the measurement apparatuses 14 may include an analysis unit configured to analyze measured information. The analysis unit may analyze biometric information using, for example, a known analyzing method. The analysis unit analyzes measured information using, for example, spectrum analysis or analysis based on an algorithm, such as a fast Fourier transform (FFT). The analysis unit may perform the same or similar analysis to one performed by the analysis unit 22 provided in the control apparatus 12. Even in the case where an analysis unit is provided in each of the measurement apparatuses 14, the analysis unit 22 may be provided in the control apparatus 12. In this case, the analysis unit 22 of the control apparatus 12 may generate new information by receiving the results of analysis performed by the measurement apparatuses 14 and further analyzing the results.

Hereinafter, a process performed by the biometric information measurement system 10 will be described in detail by citing specific examples.

First Example

Hereinafter, a process according to a first example will be described. In the first example, for example, the measurement apparatuses 14A and 14B are used. In this case, the measurement apparatus 14C may not be included in the biometric information measurement system 10.

The measurement apparatus 14A is an electroencephalograph (EEG) measurement apparatus configured to measure the EEG of a subject. The measurement apparatus 14B is a pulse measurement apparatus configured to measure the pulse rate of a subject. Here, the measurement apparatus 14A corresponds to an example of the first measurement apparatus, and the measurement apparatus 14B corresponds to an example of the second measurement apparatus. In other words, the controller 26 of the control apparatus 12 changes the condition of pulse measurement performed by the measurement apparatus 14B on the basis of the EEG measured by the measurement apparatus 14A.

Hereinafter, the first example will be described in more detail.

In response to measurement of the EEG of a subject by the measurement apparatus 14A, information indicating the measured EEG (hereinafter referred to as "EEG information") is transmitted from the measurement apparatus 14A to the control apparatus 12. As the EEG, for example, at least one of $\alpha$ waves, $\beta$ waves, $\gamma$ waves, $\theta$ waves, and $\delta$ waves are measured. These waves are classified by frequency band. The EEG information corresponds to an example of the first biometric information.

In response to measurement of the pulse rate of the subject by the measurement apparatus 14B, information indicating the measured pulse rate (hereinafter referred to as "pulse information") is transmitted from the measurement apparatus 14B to the control apparatus 12. The pulse information corresponds to an example of the second biometric information.

It is known that whether a subject who is a person is concentrated or not, and the degree of concentration may be grasped on the basis of the intensity and/or transition of $\alpha$ waves, which are EEG. The analysis unit 22 of the control apparatus 12 determines whether the subject is concentrated or not on the basis of the measured $\alpha$ waves using known technology. For example, in the case where the intensity of the measured $\alpha$ waves is included in a predetermined reference range, and that state continues for a predetermined reference time period or longer, the analysis unit 22 determines that the subject is concentrated. The reference range and the reference time period are references for determining whether the subject is concentrated or not on the basis of EEG. The analysis unit 22 generates third information indicating whether the subject is concentrated or not on the basis of α waves.

The analysis unit 22 may determine whether the subject is concentrated or not on the basis of α waves or EEG other than α waves. Hereinafter, a general relationship between EEG and the degree of concentration, and a general relationship between EEG and the sleeping state will be discussed.

γ waves: 30 Hz or greater; γ waves may be measured when the subject is unstable and excited.

β waves: 13 to 30 Hz; β waves may be measured when the subject is a little nervous and in a normal thinking state.

α waves: 7 to 13 Hz; α waves may be measured when the subject is relaxed and absorbed in something.

θ waves: 4 to 7 Hz; θ waves may be measured when the subject is in a dreaming state or a profound meditation state.

δ waves: less than or equal to 4 Hz; δ waves may be measured when the subject is not dreaming and is in a deep sleep.

Note that the above definitions, frequency ranges, and subject states are based on a general view, and the definitions, frequency ranges, and subject states are not restricted to the above details.

The analysis unit 22 may determine whether the subject is concentrated or not on the basis of each of the measured EEG. It is said that the mental state and secretion of brain hormones are closely related. For example, the "positive feedback" cycle first begins with the state of "safety and satisfaction". At this time, it is believed that brain hormones such as thyrotropin and dopamine are secreted to cause a physiological response and increase concentration. In such a cycle, α waves are generated, and a "sense of accomplishment" is born. In contrast, it is believed that adrenaline and noradrenaline are secreted in the state of "anxiety and dissatisfaction", which are opposite from "safety and satisfaction", and β waves or β waves with frequencies close to γ waves are generated, which results in a continued state of irritation. The analysis unit 22 may analyze EEG emitted from the subject to determine the state of "safety and satisfaction", "sense of accomplishment", or "anxiety and dissatisfaction".

In addition, it is known that the pulse rate increases in the case where a subject is concentrated. The analysis unit 22 of the control apparatus 12 determines whether the subject is concentrated or not on the basis of the measured pulse rate using known technology. For example, in the case where the measured pulse rate is included in a predetermined reference range, and that state continues for a predetermined reference time period or longer, the analysis unit 22 determines that the subject is concentrated. The reference range and the reference time period are references for determining whether the subject is concentrated or not on the basis of the pulse rate. The analysis unit 22 generates third information indicating whether the subject is concentrated or not on the basis of the pulse rate.

Note that the heart has a distribution of both sympathetic and parasympathetic nerves, but most of the distribution to the ventricles are sympathetic nerves. The heart rate increases when sympathetic nerves become hyperactive due to physical and/or mental stress. The relationship between the heart rate and mental stress is reported in, for example, the following documents:

(1) Lacey, J. I., Lacey, B. C.: Somatopsychic effects of interoception, Research in the Psychobiology of Human Behavior, pp. 59-73, Johns Hopkins University Press, Baltimore, 1978.

(2) Hiroaki Takatsu, Mitsuo Munakata, Osamu Ozeki, Kiyoko Yokoyama, Yosaku Watanabe, and Kazuyuki Takata: An Evaluation of the Quantitative Relationship between the Subjective Stress and Heart Rate Variability, Institute of Electrical Engineers of Japan (IEEJ) Transactions on Electronics, Information and Systems C, 120(1), 104-110, 2000.

For example, the controller 26 of the control apparatus 12 activates the measurement apparatus 14A to allow the measurement apparatus 14A to measure EEG; and the controller 26 of the control apparatus 12 deactivates the measurement apparatus 14B to not allow the measurement apparatus 14B to measure the pulse. The controller 26 may turn off the electric power of the measurement apparatus 14B, or may not allow the measurement apparatus 14B to measure the pulse while the electric power of the measurement apparatus 14B is on. The measurement apparatus 14A measures EEG, and the measurement apparatus 14A transmits EEG information to the control apparatus 12. In addition, the measurement apparatus 14B does not measure the pulse, and the measurement apparatus 14B does not transmit pulse information to the control apparatus 12.

The analysis unit 22 determines whether the subject is concentrated or not by analyzing EEG (such as α waves) indicated by the EEG information transmitted from the measurement apparatus 14A. In doing so, third information based on EEG is generated. The controller 26 may cause the display of the UI unit 18 to display the third information based on EEG, transmit the third information to an external apparatus, or store the third information in the memory 20.

In the case where the analysis unit 22 determines on the basis of EEG that the subject is concentrated, the controller 26 activates the measurement apparatus 14B to allow the measurement apparatus 14B to measure the pulse; and the controller 26 deactivates the measurement apparatus 14A to not allow the measurement apparatus 14A to measure EEG. In the case where the electric power of the measurement apparatus 14B is off, the controller 26 turns on the electric power of the measurement apparatus 14B, and allows the measurement apparatus 14B to measure the pulse. The controller 26 may turn off the electric power of the measurement apparatus 14A, or may not allow the measurement apparatus 14A to measure EEG while the electric power of the measurement apparatus 14A is on. The measurement apparatus 14B measures the pulse, and the measurement apparatus 14B transmits pulse information to the control apparatus 12. The measurement apparatus 14A does not measure EEG, and the measurement apparatus 14A does not transmit EEG information to the control apparatus 12. The controller 26 may cause the display of the UI unit 18 to display information indicating that the measurement of biometric information has switched from EEG measurement to pulse measurement.

As described above, the controller 26 controls the start timing of pulse measurement performed by the measurement apparatus 14B, which is the second measurement apparatus, on the basis of EEG information, which is the first biometric information.

The analysis unit 22 determines whether the subject is concentrated or not by analyzing the pulse rate indicated by the pulse information transmitted from the measurement apparatus 14B. In doing so, third information based on the pulse rate is generated. The controller 26 may cause the display of the UI unit 18 to display the third information based on the pulse rate, transmit the third information to an external apparatus, or store the third information in the memory 20.

In general, the amount of data of EEG is greater than the amount of data of the pulse rate, and data transmission of EEG consumes more electric power than data transmission of the pulse rate. As described above, after it is determined on the basis of EEG measurement that the subject is concentrated, measurement of biometric information is changed from EEG measurement to pulse measurement. In this way, the power consumption of the measurement apparatus 14A may be reduced while continuing the measurement for determining whether the subject is concentrated or not. In other words, the power consumption of the whole biometric information measurement system 10 may be reduced.

After the pulse measurement performed by the measurement apparatus 14B has started, the controller 26 may allow the measurement apparatus 14B to measure the pulse rate at a predetermined time interval. The analysis unit 22 may measure the length of time in which the subject is continuously concentrated on the basis of the pulse rate measured by the measurement apparatus 14B. In the case where the length of time becomes greater than or equal to a predetermined threshold, the controller 26 may cause the display of the UI unit 18 to display information indicating a warning or information for prompting the subject to take a rest, or may emit warning sound or sound for prompting the subject to take a rest from a loudspeaker provided in the control apparatus 12.

For a person to effectively work while keeping his/her concentration, it is recommended that the person take a rest after working for a certain amount of time (such as about 90 minutes). In addition, when a person continuously work for a long period of time, the person may be physically stressed. Therefore, useful information is provided to the subject by outputting the above-mentioned warning or the like.

Second Example

Hereinafter, a process according to a second example will be described. In the second example, for example, the measurement apparatuses 14A and 14B are used. In this case, the measurement apparatus 14C may not be included in the biometric information measurement system 10.

The measurement apparatus 14A is an EEG measurement apparatus configured to measure the EEG of a subject. The measurement apparatus 14B is a blood pressure measurement apparatus configured to measure the blood pressure of a subject. Here, the measurement apparatus 14A corresponds to an example of the first measurement apparatus, and the measurement apparatus 14B corresponds to an example of the second measurement apparatus. In other words, the controller 26 of the control apparatus 12 changes the condition of blood pressure measurement performed by the measurement apparatus 14B on the basis of the EEG measured by the measurement apparatus 14A.

Hereinafter, the second example will be described in more detail.

In response to measurement of EEG by the measurement apparatus 14A, EEG information indicating the measured EEG is transmitted from the measurement apparatus 14A to the control apparatus 12. The EEG information corresponds to an example of the first biometric information.

In response to measurement of blood pressure by the measurement apparatus 14B, information indicating the measured blood pressure (hereinafter referred to as "blood pressure information") is transmitted from the measurement apparatus 14B to the control apparatus 12. The blood pressure information corresponds to an example of the second biometric information.

It is known that the sleeping state of a subject who is a person may be grasped on the basis of the type, intensity, and/or transition of EEG, for example. The sleeping state is classified into, for example, rapid eye movement (REM) sleep, non-REM sleep, and awake. Needless to say, this classification is only one example, and other types of classification may be used. Here, it is assumed that, for example, in the case where the sleeping state of a subject is REM sleep or non-REM sleep, the state of the subject is a sleeping state; and, in the case where the sleeping state of the subject is awake, the state of the subject is a non-sleeping state. The analysis unit 22 of the control apparatus 12 determines the sleeping state of a subject on the basis of the type, intensity, and/or transition of measured EEG using known technology. The analysis unit 22 generates third information indicating the sleeping state of the subject on the basis of EEG.

It is known that EEG when a person falls asleep occur in the order of β waves, α waves, θ waves, and δ waves. When a subject lies down and closes his/her eyes, the body relaxes from a state in which β waves are generated, and then α waves are generated. From that stage, when the consciousness fades away, θ waves are generated, and, when the sleep gets deeper, δ waves are generated. The analysis unit 22 determines the sleeping state of the subject by analyzing EEG that occurs in this way.

For example, the controller 26 of the control apparatus 12 activates the measurement apparatus 14A to allow the measurement apparatus 14A to measure EEG; and the controller 26 of the control apparatus 12 activates the measurement apparatus 14B to allow the measurement apparatus 14B to measure the blood pressure. The measurement apparatus 14A measures EEG, and the measurement apparatus 14A transmits EEG information to the control apparatus 12. In addition, the measurement apparatus 14B measures the blood pressure, and the measurement apparatus 14B transmits blood pressure information to the control apparatus 12.

The analysis unit 22 determines whether the state of the subject is a sleeping state or not by analyzing EEG indicated by the EEG information transmitted from the measurement apparatus 14A. In other words, the analysis unit 22 determines whether the sleeping state of the subject is REM sleep, non-REM sleep, or awake by analyzing EEG. In the case where the sleeping state of the subject is REM sleep or non-REM sleep, the analysis unit 22 determines that the state of the subject is a sleeping state. In the case where the sleeping state of the subject is awake, the analysis unit 22 determines that the state of the subject is a non-sleeping state.

The analysis unit 22 determines whether the state of the subject has changed from a sleeping state to a non-sleeping state. In addition, the information generator 24 generates third information indicating the sleeping state of the subject. The controller 26 may cause the display of the UI unit 18 to display the third information indicating the sleeping state, transmit the third information to an external apparatus, or store the third information in the memory 20.

In the case where the analysis unit 22 determines that the state of the subject has changed from a sleeping state to a non-sleeping state, the controller 26 changes the time interval of blood pressure measurement performed by the measurement apparatus 14B. The controller 26 changes, for example, the time interval of blood pressure measurement after the state of the subject has changed from a sleeping state to a non-sleeping state (hereinafter referred to as a "second time interval") to be shorter than the time interval of blood pressure measurement in a state where the state of the subject is a sleeping state (hereinafter referred to as a "first time interval"). In doing so, after the subject wakes up, the blood pressure is measured more finely than when the subject is sleeping. Note that the user may change the first time interval and the second time interval while maintaining the relationship that the second time interval is shorter than the first time interval.

Alternatively, in the case where the analysis unit 22 determines that the state of the subject changed from a sleeping state to a non-sleeping state, the controller 26 may change the sensitivity of blood pressure measurement performed by the measurement apparatus 14B. The controller 26 changes, for example, the sensitivity of blood pressure measurement after the state of the subject has changed from a sleeping state to a non-sleeping state (hereinafter referred to as "second sensitivity") to be higher than the sensitivity of blood pressure measurement in a state where the state of the subject is a sleeping state (hereinafter referred to as "first sensitivity"). In doing so, after the subject wakes up, blood pressure information with higher sensitivity than when the subject is sleeping is measured. Note that the user may change the first sensitivity and the second sensitivity while maintaining the relationship that the second sensitivity is higher than the first sensitivity.

Alternatively, in the case where the analysis unit 22 determines that the state of the subject has changed from a sleeping state to a non-sleeping state, the controller 26 may change both the time interval and the sensitivity of blood pressure measurement performed by the measurement apparatus 14B. The controller 26 changes the time interval of blood pressure measurement after the state of the subject has changed from a sleeping state to a non-sleeping state to be shorter than the time interval of blood pressure measurement in a state where the state of the subject is a sleeping state. In addition, the controller 26 changes the sensitivity of blood pressure measurement after the state of the subject has changed from a sleeping state to a non-sleeping state to be higher than the sensitivity of blood pressure measurement in a state where the state of the subject is a sleeping state.

As described above, the controller 26 changes at least one of the time interval and the sensitivity of blood pressure measurement performed by the measurement apparatus 14B on the basis of EEG information, which is the first biometric information.

Note that the controller 26 may deactivate the operation of the measurement apparatus 14B while the subject is sleeping. For example, the controller 26 may turn off the electric power of the measurement apparatus 14B in the meantime. In this case, in the case where the state of the subject changes from a sleeping state to a non-sleeping state, the controller 26 turns on the electric power of the measurement apparatus 14B and allows the measurement apparatus 14B to measure the blood pressure. In addition, in the case where blood pressure measurement performed by the measurement apparatus 14B has started, the controller 26 may stop EEG measurement performed by the measurement apparatus 14A. The controller 26 may turn off the electric power of the measurement apparatus 14A.

Generally, blood pressure fluctuates throughout the day, as it becomes lower during sleeping and becomes higher after waking up. It is believed that blood pressure becomes higher in the morning because sympathetic nerves that activate the movement of the heart start moving. In addition, a sudden increase in blood pressure is believed to cause strokes or the like. For example, since it is said that myocardial infarction attacks are most likely to occur after waking up, it is necessary to pay special attention to high blood pressure in the morning, and it is meaningful to measure the blood pressure at the time of waking up. Regarding this point, useful information is provided to the subject by controlling the condition of blood pressure measurement, as described above.

Note that the controller 26 may cause the display of the UI unit 18 to display EEG information measured by the measurement apparatus 14A, or may cause the display of the UI unit 18 to display blood pressure information measured by the measurement apparatus 14B.

Instead of an EEG measurement apparatus, an acceleration sensor that measures acceleration may be used. In this case, the measurement apparatus 14A is an acceleration sensor that measures acceleration, and the measurement apparatus 14B is a blood pressure measurement apparatus. The measurement apparatus 14A corresponds to an example of the first measurement apparatus, and the measurement apparatus 14B corresponds to an example of the second measurement apparatus. In other words, the controller 26 of the control apparatus 12 changes the condition of blood pressure measurement performed by the measurement apparatus 14B on the basis of the acceleration measured by the measurement apparatus 14A.

In response to measurement of acceleration by the measurement apparatus 14A, acceleration information indicating the measured acceleration is transmitted from the measurement apparatus 14A to the control apparatus 12. In addition, blood pressure information is transmitted from the measurement apparatus 14B to the control apparatus 12. The acceleration information corresponds to an example of the first biometric information, and the blood pressure information corresponds to an example of the second biometric information.

When the measurement apparatus 14A, which is an acceleration sensor, is worn by the subject, the subject's acceleration, that is, movement, is measured. It is known that the sleeping state of a subject who is a person may be grasped on the basis of the intensity and/or the amount of change of acceleration. The analysis unit 22 of the control apparatus 12 determines the sleeping state of a subject on the basis of the measured acceleration using known technology. For example, in the case where the intensity of the measured acceleration is included in a predetermined reference range, and that state continues for a predetermined reference time period or longer, the analysis unit 22 determines that the state of the subject is a sleeping state. Otherwise, the analysis unit 22 determines that the state of the subject is a non-sleeping state. The reference range and the reference time period are references for determining whether the subject is sleeping or not on the basis of the intensity of acceleration. The analysis unit 22 generates third information indicating whether the state of the subject is a sleeping state or not on the basis of the acceleration.

In addition, in the case where a change of the measured acceleration is included in a predetermined reference range, and that state continues over a predetermined reference time period, the analysis unit 22 may determine that the state of the subject is a sleeping state.

In the case where the analysis unit 22 determines on the basis of the acceleration that the state of the subject has changed from a sleeping state to a non-sleeping state, the controller 26 changes at least one of the time interval and the sensitivity of blood pressure measurement performed by the measurement apparatus 14B, as described above.

In yet another example, the analysis unit 22 may determine whether the state of the subject is a sleeping state or an awaken state on the basis of EEG or acceleration. A sleeping state is a state in which the subject is in bed, and an awaken state is a state in which the subject has gotten out of bed. In the case where the state of the subject changes from sleeping to awaken, the controller 26 may change at least one of the time interval and the sensitivity of blood pressure measurement performed by the measurement apparatus 14B.

Third Example

Hereinafter, a process according to a third example will be described. In the third example, for example, the measurement apparatuses 14A, 14B, and 14C are used.

The measurement apparatus 14A is an EEG measurement apparatus. The measurement apparatus 14B is a heart rate measurement apparatus that measures the heart rate of a subject. The measurement apparatus 14C is an acceleration sensor for measuring the movement of a subject. Here, the measurement apparatus 14C corresponds to an example of the first measurement apparatus, and the measurement apparatuses 14A and 14B correspond to examples of the second measurement apparatuses. In other words, the controller 26 of the control apparatus 12 changes the condition of EEG measurement performed by the measurement apparatus 14A and the condition of heart rate measurement performed by the measurement apparatus 14B on the basis of acceleration measured by the measurement apparatus 14C.

Hereinafter, the third example will be described in more detail.

In response to measurement of EEG by the measurement apparatus 14A, EEG information indicating the measured EEG is transmitted from the measurement apparatus 14A to the control apparatus 12. The EEG information corresponds to an example of the second biometric information.

In response to measurement of heart rate by the measurement apparatus 14B, heart rate information indicating the measured heart rate is transmitted from the measurement apparatus 14B to the control apparatus 12. The heart rate information corresponds to an example of the second biometric information.

In response to measurement of acceleration by the measurement apparatus 14C, acceleration information indicating the measured acceleration is transmitted from the measurement apparatus 14C to the control apparatus 12. The acceleration information corresponds to an example of the first biometric information.

The analysis unit 22 detects the movement of the subject on the basis of the intensity and/or change of acceleration indicated by the acceleration information. For example, in the case where the intensity of acceleration is greater than or equal to a predetermined threshold, the analysis unit 22 determines that the subject is moving. In the case where the intensity of acceleration is less than the threshold, the analysis unit 22 determines that the subject remains still. In addition, in the case where the intensity of acceleration is greater than or equal to a predetermined threshold, and that state continues for a predetermined reference time period or longer, the analysis unit 22 may determine that the subject is moving. Otherwise, the analysis unit 22 may determine that the subject remains still. Alternatively, in the case where the amount of change of acceleration is greater than or equal to a predetermined threshold, the analysis unit 22 may determine that the subject is moving. In the case where the amount of change of acceleration is less than the threshold, the analysis unit 22 may determine that the subject remains still. In the case where the amount of change of acceleration is greater than or equal to a predetermined threshold, and that state continues for a predetermined reference time period or longer, the analysis unit 22 may determine that the subject is moving. Otherwise, the analysis unit 22 may determine that the subject remains still.

The analysis unit 22 may generate information indicating the subject's mental stress on the basis of EEG. In addition, the analysis unit 22 may generate information indicating the subject's dynamic stress (that is, physical stress) on the basis of heart rate. The information indicating the mental stress and the information indicating the dynamic stress correspond to examples of the third information.

For example, the controller 26 of the control apparatus 12 activates the measurement apparatus 14C to allow the measurement apparatus 14C to measure acceleration. The analysis unit 22 determines whether the subject is moving or not on the basis of acceleration.

In the case where the analysis unit 22 determines that the subject remains still, the controller 26 allows the measurement apparatus 14A to start EEG measurement, and allows the measurement apparatus 14B to end the heart rate measurement. The controller 26 may turn off the electric power of the measurement apparatus 14B.

In the case where the analysis unit 22 determines that the subject is moving, the controller 26 allows the measurement apparatus 14A to end the EEG measurement, and allows the measurement apparatus 14B to start heart rate measurement. The controller 26 may turn off the electric power of the measurement apparatus 14A.

As described above, the controller 26 controls the start timing and the end timing of EEG measurement performed by the measurement apparatus 14A, which is the second measurement apparatus, on the basis of acceleration information, which is the first biometric information. Similarly, the controller 26 controls the start timing and the end timing of heart rate measurement performed by the measurement apparatus 14B, which is the second measurement apparatus, on the basis of acceleration information, which is the first biometric information.

In another example, regardless of whether the subject is moving or not, the controller 26 may turn on the electric power of each of the measurement apparatuses 14A, 14B, and 14C, and allow the measurement apparatus 14A to measure EEG, the measurement apparatus 14B to measure heart rate, and the measurement apparatus 14C to measure acceleration.

In this case, in the case where the analysis unit 22 determines that the subject remains still, the controller 26 shortens the time interval of EEG measurement performed by the measurement apparatus 14A, and elongates the time interval of heart rate measurement performed by the measurement apparatus 14B. In the case where the analysis unit 22 determines that the subject is moving, the controller 26 elongates the time interval of EEG measurement performed by the measurement apparatus 14A, and shortens the time interval of heart rate measurement performed by the measurement apparatus 14B. In other words, the time interval of EEG measurement when the subject remains still is shorter than the time interval of EEG measurement when the subject is moving. In addition, the time interval of heart rate measurement when the subject remains still is longer than the time interval of heart rate measurement when the subject is moving.

In another example, in the case where the analysis unit 22 determines that the subject remains still, the controller 26 may increase the sensitivity of EEG measurement performed by the measurement apparatus 14A, and decrease the sensitivity of heart rate measurement performed by the measurement apparatus 14B. In the case where the analysis unit 22 determines that the subject is moving, the controller 26 may decrease the sensitivity of EEG measurement performed by the measurement apparatus 14A, and increase the sensitivity of heart rate measurement performed by the measurement apparatus 14B. In other words, the sensitivity of EEG measurement when the subject remains still is higher than the sensitivity of EEG measurement when the subject is moving. In addition, the sensitivity of heart rate measurement when the subject remains still is lower than the sensitivity of heart rate measurement when the subject is moving.

In yet another example, in the case where the analysis unit 22 determines that the subject remains still, the controller 26 may shorten the time interval of EEG measurement performed by the measurement apparatus 14A and increase the sensitivity of EEG measurement performed by the measurement apparatus 14A, and may elongate the time interval of heart rate measurement performed by the measurement apparatus 14B and decrease the sensitivity of heart rate measurement performed by the measurement apparatus 14B. In the case where the analysis unit 22 determines that the subject is moving, the controller 26 may elongate the time interval of EEG measurement performed by the measurement apparatus 14A and decrease the sensitivity of EEG measurement performed by the measurement apparatus 14A, and may shorten the time interval of heart rate measurement performed by the measurement apparatus 14B and increase the sensitivity of heart rate measurement performed by the measurement apparatus 14B.

In addition, the information generator 24 may generate new information indicating comprehensive stress on the basis of information indicating mental stress and information indicating dynamic stress. The new information corresponds to an example of the third information.

Modification

Figure 2:
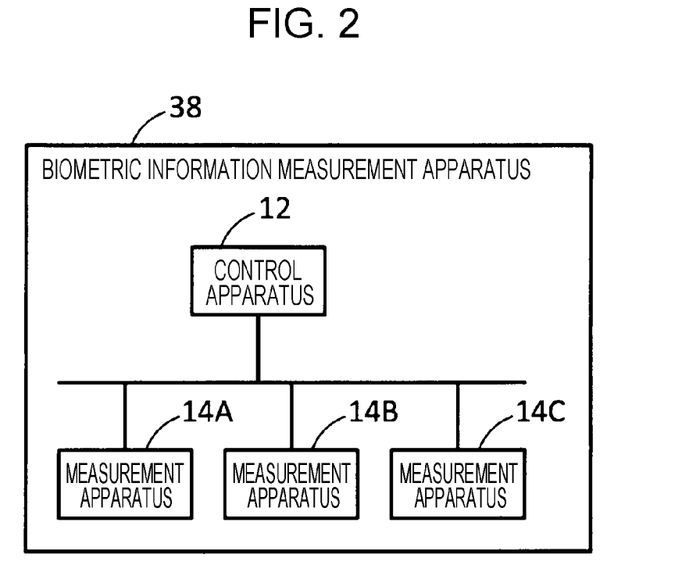
FIG. 2 is a block diagram illustrating the configuration of a biometric information measurement apparatus according to the exemplary embodiment of the present disclosure.

Although the control apparatus 12 and the measurement apparatuses 14A, 14B, and 14C are separate apparatuses in the above-described exemplary embodiment, these apparatuses may constitute one apparatus. For example, as illustrated in FIG. 2, a biometric information measurement apparatus 38 according to a modification includes the control apparatus 12 and the measurement apparatuses 14A, 14B, and 14C.

Needless to say, the biometric information measurement apparatus 38 may include at least one measurement apparatus 14 among the measurement apparatuses 14A, 14B, and 14C. In the case where the number of measurement apparatuses 14 included in the biometric information measurement apparatus 38 is one, this measurement apparatus 14 included in the biometric information measurement apparatus 38 is used as the first measurement apparatus or one of the second measurement apparatuses, and another measurement apparatus 14 not provided in the biometric information measurement apparatus 38 is used as the first measurement apparatus or the other one of the second measurement apparatuses.

The functions of the individual units of the above-described control apparatus 12, measurement apparatuses 14A, 14B, and 14C, and biometric information measurement apparatus 38 are realized by, for example, cooperation between hardware and software. Specifically, the control apparatus 12, the measurement apparatuses 14A, 14B, and 14C, and the biometric information measurement apparatus 38 each include one or more processors such as central processing units (CPUs) (not illustrated). The functions of the units of the control apparatus 12, the measurement apparatuses 14A, 14B, and 14C, and the biometric information measurement apparatus 38 are realized by reading and executing, by this one or more processors, a program stored in a storage device (not illustrated). The program is stored in the storage device via a recording medium such as a compact disc (CD) or a digital versatile disc (DVD) or via a communication channel such as a network. In another example, the functions of the units of the control apparatus 12, the measurement apparatuses 14A, 14B, and 14C, and the biometric information measurement apparatus 38 may be realized by hardware resources such as a processor, an electronic circuit, or an application specific integrated circuit (ASIC). A device such as memory may be used in realizing the functions. In yet another example, the functions of the units of the control apparatus 12, the measurement apparatuses 14A, 14B, and 14C, and the biometric information measurement apparatus 38 may be realized by a digital signal processor (DSP), a field programmable gate array (FPGA), or the like.

The foregoing description of the exemplary embodiment of the present disclosure has been provided for the purposes of illustration and description. It is not intended to be exhaustive or to limit the disclosure to the precise forms disclosed. Obviously, many modifications and variations will be apparent to practitioners skilled in the art. The embodiment was chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. A biometric information measurement system, comprising:
 a first measurement apparatus that measures first biometric information of a subject;
 a second measurement apparatus that measures second biometric information which is biometric information of the subject and which is different from the first biometric information; and
 a control apparatus that controls operation of each of the first and second measurement apparatuses and changes a condition of measurement performed by the second measurement apparatus on the basis of the first biometric information,
 wherein the control apparatus is configured to activate the first measurement apparatus while deactivating the second measurement apparatus or to activate the second measurement apparatus while deactivating the first measurement apparatus.

2. The biometric information measurement system according to claim 1, wherein the condition of measurement is a time interval of measurement performed by the second measurement apparatus.

3. The biometric information measurement system according to claim 2, wherein the control apparatus further controls output of third information based on the first biometric information and the second biometric information.

4. The biometric information measurement system according to claim 1, wherein the condition of measurement is sensitivity of measurement performed by the second measurement apparatus.

5. The biometric information measurement system according to claim 4, wherein the control apparatus further controls output of third information based on the first biometric information and the second biometric information.

6. The biometric information measurement system according to claim 1, wherein the condition of measurement is at least one of start timing and end timing of measurement performed by the second measurement apparatus.

7. The biometric information measurement system according to claim 6, wherein the control apparatus further controls output of third information based on the first biometric information and the second biometric information.

8. The biometric information measurement system according to claim 1, wherein the control apparatus further controls output of third information based on the first biometric information and the second biometric information.

9. The biometric information measurement system according to claim 1, wherein the control apparatus is configured to activate or deactivate the second measurement apparatus according to a sleeping state of the subject, and the sleeping state of the subject is determined by analyzing the first biometric information.

10. A biometric information measurement apparatus comprising:
   a first measurement unit that measures first biometric information of a subject;
   a second measurement unit that measures second biometric information which is biometric information of the subject and which is different from the first biometric information; and
   a controller that controls operation of each of the first and second measurement units and changes a condition of measurement performed by the second measurement unit on the basis of the first biometric information,
   wherein the controller is configured to activate the first measurement unit while deactivating the second measurement unit or to activate the second measurement unit while deactivating the first measurement unit.

11. The biometric information measurement apparatus according to claim 10, wherein the controller is configured to activate or deactivate the second measurement unit according to a sleeping state of the subject, and the sleeping state of the subject is determined by analyzing the first biometric information.

12. A biometric information measurement system comprising:
   first measurement means for measuring first biometric information of a subject;
   second measurement means for measuring second biometric information which is biometric information of the subject and which is different from the first biometric information; and
   control means for controlling operation of each of the first and second measurement means and changing a condition of measurement performed by the second measurement means on the basis of the first biometric information,
   wherein the control means is configured to activate the first measurement means while deactivating the second measurement means or to activate the second measurement means while deactivating the first measurement means.

13. The biometric information measurement system according to claim 12, wherein the control means is configured to activate or deactivate the second measurement means according to a sleeping state of the subject, and the sleeping state of the subject is determined by analyzing the first biometric information.

* * * * *